US008895084B2

(12) United States Patent
Worrell et al.

(10) Patent No.: US 8,895,084 B2
(45) Date of Patent: Nov. 25, 2014

(54) **ORAL CARE COMPOSITION CONTAINING EXTRACT OF UNOXIDIZED *CAMELLIA***

(75) Inventors: Cortney L. Worrell, Plainfield, NJ (US); Harsh M. Trivedi, Somerset, NC (US); Kimberlee Panaligan, Parlin, NJ (US); Tao Xu, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 34 days.

(21) Appl. No.: 11/256,860

(22) Filed: Oct. 24, 2005

(65) Prior Publication Data

US 2006/0141073 A1 Jun. 29, 2006

Related U.S. Application Data

(60) Provisional application No. 60/639,079, filed on Dec. 23, 2004, provisional application No. 60/639,080, filed on Dec. 23, 2004.

(51) Int. Cl.

| | | |
|---|---|---|
| *A61K 8/02* | (2006.01) | |
| *A61K 36/82* | (2006.01) | |
| *A61K 31/075* | (2006.01) | |
| *A61Q 11/00* | (2006.01) | |
| *A61K 8/97* | (2006.01) | |
| *A61K 8/49* | (2006.01) | |

(52) U.S. Cl.
CPC . *A61Q 11/00* (2013.01); *A61K 8/97* (2013.01); *A61K 8/498* (2013.01)
USPC ............. 424/729; 424/401; 424/435; 424/49; 424/58; 514/721

(58) Field of Classification Search
CPC .... A61K 31/075; A61K 36/82; A61K 31/353
USPC ............... 424/729, 401, 435, 49, 58; 514/721
See application file for complete search history.

(56) References Cited

U.S. PATENT DOCUMENTS

| | | | |
|---|---|---|---|
| 3,122,565 A | 2/1964 | Kijima et al. | |
| 4,550,183 A | 10/1985 | Willging | |
| 4,894,220 A | 1/1990 | Nabi et al. | |
| 5,080,887 A | 1/1992 | Gaffar et al. | |
| 5,292,526 A | 3/1994 | Gaffar et al. | |
| 5,538,715 A | 7/1996 | Gaffar et al. | |
| 5,681,548 A | 10/1997 | Esposito et al. | |
| 5,683,678 A | 11/1997 | Heckert et al. | |
| 5,723,500 A | 3/1998 | Stringer et al. | |
| 5,776,435 A | 7/1998 | Gaffar et al. | |
| 5,912,274 A | 6/1999 | Stringer et al. | |
| 6,149,894 A * | 11/2000 | Yamane et al. | 424/49 |
| 6,290,933 B1 | 9/2001 | Durga et al. | |
| 6,403,059 B1 | 6/2002 | Martin et al. | |
| 6,495,170 B1 * | 12/2002 | Smit et al. | 424/725 |
| 6,500,409 B1 * | 12/2002 | Scherl et al. | 424/58 |
| 6,685,921 B2 | 2/2004 | Lawlor | |
| 2003/0206874 A1 | 11/2003 | Doyle et al. | |
| 2003/0235606 A1 | 12/2003 | Nussen | |
| 2003/0235630 A1 | 12/2003 | Nussen | |
| 2005/0025719 A1 | 2/2005 | Nussen | |
| 2005/0079140 A1 | 4/2005 | Nussen | |
| 2006/0134286 A1 * | 6/2006 | Maeda | 426/335 |

FOREIGN PATENT DOCUMENTS

| | | |
|---|---|---|
| CN | 1373652 | 10/2002 |
| EP | 1 002 524 | 5/2000 |
| EP | 1 072 254 | 1/2001 |
| JP | 61 197510 | 1/1987 |
| RU | 2066180 | 9/1996 |
| RU | 2203032 | 4/2003 |
| RU | 2 241 437 | 12/2004 |
| WO | WO 96/28178 | 9/1996 |
| WO | WO 98/41096 | 9/1998 |
| WO | WO 01/17494 | 3/2001 |
| WO | WO 01/85116 | 11/2001 |
| WO | WO 03/094878 | * 11/2003 |
| WO | WO 2004/073671 | 9/2004 |

OTHER PUBLICATIONS

Translation of WO 03/094878—Nov. 2003.*
Hamilton-Miller, 2001, "Anti-cariogenic properties of tea (*Camellia sinensis*)," J. Med. Microbiol. 50(4):299-302.
Makimura et al., 1993, "Inhibitory effect of tea catechins on collagenase activity," J. Periodontol. 64(7):630-636.
Rasheed et al., 1998, "Antibacterial activity of *Camellia sinensis* extracts against dental caries," Arch. Pharmaceutical Research 21(3):348-352.
Sakanaka et al., 1989, "Antibacterial Substances in Japanese Green Tea Extract against *Streptococcus mutans*, a Cariogenic Bacterium," Agricultural Biol. Chem. 53(9):2307-2311.
Traditional Knowledge Digital Library, Akrob, 1887
Traditional Knowledge Digital Library, Chai, 1911.
Wolinsky et al., 2000, "A comparative pilot study of the effects of a dentifrice containing green tea bioflavonoids, sanguinarine or triclosan on oral bacterial biofilm formation," J. Clin. Dent. 11(2):53-59.

* cited by examiner

*Primary Examiner* — Susan Hoffman
(74) *Attorney, Agent, or Firm* — Anne Louise St. Martin

(57) ABSTRACT

An oral composition for at least one or treating and inhibiting an oral inflammatory condition comprising:
a *Camellia* extract including at least about 30% epigallocatechin gallate, at least about 50% total catechins, and at least about 60% total polyphenols; and
a substantially water insoluble non-cationic anti-bacterial agent.

13 Claims, No Drawings

ORAL CARE COMPOSITION CONTAINING EXTRACT OF UNOXIDIZED *CAMELLIA*

CROSS REFERENCE TO RELATED APPLICATIONS

The application claims priority to U.S. Provisional Patent Application Ser. Nos. 60/639,079 and 60/639,080, each filed on Dec. 23, 2004, the contents of each of which are incorporated herein by reference.

BACKGROUND OF THE INVENTION

Oral inflammations, such as gingivitis and periodontitis, are common oral conditions. Gingivitis, which is an inflammation of the gums, is the initial stage of gum disease. The direct cause of gingivitis is plaque, which is a soft, sticky, colorless film including bacteria that forms on the teeth and gums. Plaque, if left untreated, produces toxins that can inflame or infect the gum tissue to cause gingivitis. Untreated gingivitis can eventually spread from the gums to the ligaments and bone that support the teeth, thus causing periodontitis. While a variety of different treatments exist for preventing and suppressing oral inflammatory conditions, such treatments are subject to improvement.

Antioxidants are compounds that help inhibit oxidation reactions caused by active or free radical oxygen. Active oxygen naturally occurs in the body as a result of chemical reactions during normal cellular processes. Active oxygen can also be formed in response to excess pollution, too much UV sunlight, and exposure to cigarette smoke. In an attempt to stabilize, active oxygen molecules bond with other molecules of the body to oxidize them, which leads to, for example, destruction of cell membranes, damage to DNA, and oxidation of lipids (fats). Oxidation can ultimately lead to cancer, heart disease, stroke, rheumatoid arthritis, cataracts, and Alzheimer's disease.

Antioxidants can inhibit oxidation reactions in a number of different ways. For example, antioxidants can scavenge reactive oxygen free radical species and/or decrease localized oxygen concentration thereby reducing molecular oxygen's oxidation potential. Various antioxidants exist and antioxidants can be derived from a variety of different sources. Exemplary antioxidants include Vitamin E, Vitamin C, carotenoids, and polyphenols, such as flavonoids.

BRIEF SUMMARY OF THE INVENTION

In an embodiment of the present invention, an oral composition for at least one or treating and inhibiting an oral inflammatory condition is provided. The oral composition comprises: a *Camellia* extract including at least about 30% epigallocatechin gallate, at least about 50% total catechins, and at least about 60% total polyphenols; and a substantially water insoluble non-cationic anti-bacterial agent.

In another embodiment of the present invention, a method of at least one of treating and inhibiting an oral inflammatory condition is provided. The method comprises administering to an oral cavity of a subject in need thereof an effective amount of an oral composition comprising a *Camellia* extract including at least about 30% epigallocatechin gallate, at least about 50% total catechins, and at least about 60% total polyphenols.

In yet another embodiment of the present invention, a method of at least one of treating and inhibiting an oral inflammatory condition and providing antioxidant activity in an oral cavity is provided. The method includes administering to an oral cavity of a human or other animal subject in need thereof an effective amount of an oral composition comprising: a *Camellia* extract including at least about 30% epigallocatechin gallate, at least about 50% total catechins, and at least about 60% total polyphenols; and a halogenated diphenyl ether anti-bacterial agent.

In various embodiments, the compositions and methods of the present invention further comprise an anti-bacterial agent, such as triclosan. In various embodiments, the compositions and methods further comprise a rosemary extract.

It has been discovered that compositions and methods of this invention afford advantages over anti-inflammatory and antioxidant compositions and methods among those known in the art. Such advantages include the use of an oral composition including a natural green tea extract to provide enhanced anti-inflammatory activity and enhanced anti-oxidant activity. Further uses, benefits, and embodiments of the present invention are apparent from the description set forth herein.

DETAILED DESCRIPTION OF THE INVENTION

Oral compositions according to the present invention comprise an extract obtained from tissue of a member of the genus *Camellia*. The compositions of the invention may exhibit an anti-inflammatory and/or antioxidant effect when introduced to the oral cavity. This anti-inflammatory and/or antioxidant activity may be increased when the oral compositions of the invention also include other antibacterial agents, such as triclosan and/or rosemary extract.

The present invention, in various embodiments, can provide oral compositions for treating and/or inhibiting oral inflammation and for introducing an antioxidant activity to the oral cavity. The oral composition may take any dosage form useful for oral administration. Illustrative examples of these include: a dentifrice, e.g., a toothpaste, dental gel, dental cream, or tooth powder; a mouthwash, mouth rinse, or mouth spray; an oral slurry or liquid dentifrice; a gum or other confectionary; a lozenge; dental floss or dental tape; a prophylaxis paste or powder; a mono- or multi-layer oral film or gel strip, e.g., tooth strips or breath strips, preferably using a biodegradable or orally consumable film or gel; functional film or gel flakes or functional milli-, micro-, or nano-particles; a film-forming composition comprising pre-gel(s) or pre-polymer(s), e.g., film-forming dentifrices, dental paints; a tooth hardener; or a coating on an oral, e.g., orthodontic, appliance or implant.

The present invention provides oral compositions comprising *Camellia* extract. The *Camellia* extract is obtained from substantially unoxidized plant tissues, of the genus *Camellia*. Any variety, form, or subspecies of genus *Camellia* may be used although extracts of unoxidized *Camellia sinensis* may be preferred. Also preferred may be the subspecies or variants: *C. sinensis* var. *assamica*, *C. assamica* and var. *kucha*; *C. sinensis* var. *cambodiensis*, subsp. *lasiocalyx* and var. Shan; *C. sinensis* var. *dehungensis*; *C. sinensis* var. *pubilimba*; and *C. sinensis* var. *sinensis, bohea, macrophylla, parvifolia,* and *waldenae*.

In a preferred embodiment, the *Camellia* extract may be obtained from the substantially unoxidized tissue(s) of *C. sinensis* var. *assamica, C. sinensis* var. *cambodiensis*, or *C. sinensis* var. *sinensis*; in a preferred embodiment, the extract will be made from substantially unoxidized tissue(s) of *C. sinensis* var. *assamica* or *C. sinensis* var. *sinensis*; in a preferred embodiment, the extract may be obtained from a substantially unoxidized tissue(s) of *C. sinensis* var. *sinensis*. Regardless of the source, leaf tissue may be preferred, although any of leaf buds; flowers, flower buds; stems, twigs; stem, twig, and trunk bark; roots; root bark; and other aerial and reproductive parts and combinations of the same my be used.

The *Camellia* extract may be in any form, including powder, suspension, emulsion and/or an oil.

*Camellia* tissue(s) used for production of any extract for use in the invention may be prepared by any means known in the art. For example, if using leaves, the leaves should be harvested while still green in color and heated very soon after they have been picked, e.g., before about thirty minutes, more commonly before about ten minutes post-harvest. The heating can be performed by any mechanism: pan-firing, steaming, roasting, microwaving, so long as the temperature is rapidly raised (in about 5-15 minutes or less) to a level at which the catabolic enzymes present in the tissue are substantially denatured. After this heating step, the leaves may be air dried, or otherwise dehydrated.

The plant tissues processed in the above described way or in any other manner may be extracted using any suitable known extraction technique to provide an extract useful in the present invention. For example, extraction techniques that can be used include any suitable aqueous extraction or organic solvent extraction. Preferred extraction techniques utilize water, methanol, water/methanol, dichloromethane and methanol:THF. Any other suitable extraction technique may be used, such as steam distillation and supercritical fluid extraction.

The *Camellia* extract may be present in the oral composition in various amounts. Preferably, the *Camellia* extract is present in an amount greater than about 0.001%; preferably from about 0.001% to about 20%; preferably from about 0.01% to about 15%; preferably from about 0.05% to about 10%; preferably from about 0.05% to about 5%; preferably from about 0.05% to about 1%; and preferably from about 0.1% to about 0.2%.

The invention may also include vitamin (tocopherol) and/or derivatives, or analogs of the same. For example, tocopherols of the present invention include substances that have the biological and physiological activities of Vitamin E, including alpha-, beta-, gamma-, delta-, epsilon-, zeta- and eta-tocopherols of natural d- and synthetic dl-forms; substituted tocols in which one, two or three of the methyl groups in the 5, 7 and 8 positions of the chroman nucleus of tocol are replaced by a radical or radicals, such as alkyl, haloalkyl, hydroxyalkyl, aminoalkyl, acyl and allyl radicals, and in which the methyl group in the 2 position of the chroman nucleus of the tocol is replaced by a lower alkyl radical, such as ethyl, propyl and butyl; and tocopherol analogous substances such as nor-tocopherol in which the isoprene units in the 2 position of the croman nucleus are two in number, homo-tocopherol in which the isoprene units are four in number and iso-tocopherol in which a side chain composed of three isoprene units in the tocol is linear.

While the oral composition of the present invention can include any suitable natural or synthetic Vitamin E tocopherol, Vitamin E (dl-α tocopherol) ($C_{29}H_{50}O_2$, mw 430.72) is preferred. Vitamin E is available from various different sources, such as Royal DSM N.V. of The Netherlands. Vitamin E can be present in the oral composition at various different levels. For example, Vitamin E can be present in an effective amount to provide antioxidant efficacy. For example, Vitamin E can be present from about 10 to about 10,000 ppm, from about 15 to about 40 ppm, from about 20 to 30 ppm, or about 25 ppm. Also, Vitamin E can be present in the oral composition greater than about 0.001%, from about 0.001% to about 5%, from about 0.01% to about 5%, from about 0.2% to about 4%, and from about 0.3% to about 3%.

The oral composition of the invention may include one or more additional therapeutic agents, such as anti-bacterial agents or anti-inflammatory agents. Exemplary antibacterial agents may include halogenated diphenyl ethers, benzoic esters, halogenated carbanilides, 8-hydroxyquinoline and salts thereof; zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); bisguanides, such as chlorhexidine digluconate, hexetidine, octenidine, and alexidine; halogenated bisphenolic compounds, such as 2,2'methylenebis-(4-chloro-6-bromophenol); benzalkonium chloride; salicylanilide, halogenated salicylanilides; domiphen bromide; iodine; sulfonamides; bisbiguanides; phenolic compounds such as phenol and its homologs, mono- and polyalkyl and aralkyl halophenols, and bisphenolic compounds; piperidino derivatives such as delmopinol and octapinol; magnolia extract; grapeseed extract; thymol; eugenol; menthol; geraniol; carvacrol; citral; eucalyptol; catechol; 4-allylcatechol; resorcinol and its derivatives, such as hexyl resorcinol; methyl salicylate; antibiotics such as augmentin, amoxicillin, tetracycline, doxycycline, minocycline, metronidazole, neomycin, kanamycin and clindamycin; and mixtures thereof. A further illustrative list of agents is provided in U.S. Pat. Nos. 5,776,435; 5,681,548; 5,912,271 and 5,723,500, then contents of each of which are incorporated herein by reference.

The oral composition can, and preferably will, also include one or more solubilizing agents to solubilize the *Camellia* extract. The solubilizing agent can be any solubilizing agent that is effective to solubilize *Camellia* extract. For example, in various embodiments the solubilizing agent can be at least one of an orally acceptable surfactant, flavoring oil, alcohol, and solubilizing humectant (e.g., propylene glycol).

Examples of surfactants that can be used include anionic, nonionic, amphoteric, zwitterionic, and cationic synthetic detergents. Anionic surfactants include the water-soluble salts of alkyl sulfates having 8-20 carbon atoms in the alkyl radical (such as sodium alkyl sulfate), a monoalkyl phosphate compound having 6-18 carbon atoms, the water-soluble salts of sulfonated monoglycerides of fatty acids having from 8-20 carbon atoms (such as sodium lauryl sulfate (>82% pure) and sodium coconut monoglyceride sulfonates), an alkyl glycoside that is mono[alkyl($C_{12}$-$C_{22}$)]-[(Glyc)1-20], sarcosinates (such as sodium and potassium salts of lauroyl sarcosinate, myristoyl sarcosinate, palmitoyl sarcosinate, stearoyl sarcosinate and oleoyl sarcosinate), taurates, higher alkyl sulfoacetates (such as sodium lauryl sulfoacetate), isothionates (such as sodium lauroyl isothionate), sodium laureth carboxylate, sodium dodecyl benezesulfonate, and mixtures of the foregoing. Preferred are the sarcosinates since they inhibit acid formation in the mouth due to carbohydrate breakdown. Nonionic surfactants include poloxamers; polyoxyethylene sorbitan esters; fatty alcohol ethoxylates; polyethylene oxide condensates of alkyl phenols; products derived from the condensation of ethylene oxide with fatty acids, fatty alcohols, fatty amides, or polyhydric alcohols; and polypropyleneoxide or ethylene oxide condensates of aliphatic alcohols; long-chain tertiary amine oxides; long-chain tertiary phospine oxides; long-chain dialkyl sulfoxides; and mixtures of such materials. Amphoteric surfactants include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials. Zwitterionic surfactants include derivatives of aliphatic quaternary ammonium, phosphonium and sulfonium compounds in which the aliphatic radical can be a straight or branched chain and wherein one of the aliphatic substituents contains about 8-18 carbon atoms and one contains an anionic water-solubilizing group (such as carboxy, sulfonate, sulfate, phosphate or phosphonate). Cationic surfactants include aliphatic quaternary ammonium compounds having one long alkyl chain containing about 8-18 carbon atoms (such as lauryl trimethylammonium chloride, cetylpyridinium chloride, cetyltrimethylammonium bromide, diisobuytylphenoxyethyldimethylbenzylammonium chloride, coconut alkyltrimetylammonium nitrite, cetylpyridinium fluoride). Certain cationic surfactants can also act as antimicrobials.

The solubilizing agent(s) are preferably present at about 0.02% to about 50% by weight of the composition.

The oral composition can also optionally include an enhancing agent (EA) that is a water soluble or swellable anionic polymer or co-polymer comprising delivery enhancing groups and retention enhancing groups. The delivery enhancing groups enhance delivery of the *Camellia* extract to teeth and oral tissue. The retention enhancing groups enhance retention by the teeth and the oral tissue of the *Camellia* extract. The enhancing agents of the present invention can include those that are characterized as having utility as denture adhesives or fixatives or dental cements. The enhancing agent is a polymer or copolymer, which terms are entirely generic, thus including for example oligomers, homopolymers, copolymers of two or more monomers, ionomers, block copolymers, graft copolymers, cross-linked polymers and copolymers, and the like. The EA may be natural or synthetic, and water (saliva) soluble or swellable (hydratable, hydrogel forming) polymer or copolymer. The EA can be selected to have various sizes, such as an (weight) average molecular weight (MW) of: about 100 to about 1,000,000; about 1,000 to about 1,000,000; or about 2,000 to about 2,500, or from about 250,000 to about 500,000. Also, the delivery enhancing groups of the EA can be any of those listed in U.S. Pat. Nos. 5,538,715 and 5,776,435, the contents of each of which are incorporated by reference.

The delivery-enhancing group refers to one that attaches or substantively, adhesively, cohesively or otherwise bonds the EA, carrying components of the *Camellia* extract to oral (e.g. tooth and gum) surfaces, thereby "delivering" the components to such surfaces. The organic retention-enhancing group, which is generally hydrophobic, attaches or otherwise bonds the *Camellia* extract to the EA, thereby promoting retention of the *Camellia* extract directly on the EA and indirectly on the oral surface(s). In some instances, attachment of the *Camellia* extract may alternatively or additionally occur through physical entrapment thereof by the EA, especially when the EA is a cross-linked polymer, the structure of which inherently provides increased sites for such entrapment. The presence of a higher molecular weight, more hydrophobic cross-linking moiety in the cross-linked polymer still further promotes the physical entrapment of the *Camellia* extract in or on the cross-linked EA polymer.

The oral compositions comprise an orally acceptable vehicle. Any suitable orally acceptable vehicle can be used, such as those described in U.S. Pat. No. 4,894,220 titled "Antibacterial Anti-Plaque Oral Composition," which is incorporated by reference herein. For example, the vehicle can include a water-phase with humectant. In the present invention, the water and humectant liquid phase can comprise at least about 10% by weight of the oral composition. Moreover, preferably the humectant comprises propylene glycol, which can help to solubilize the *Camellia* extract. The remainder of the humectant is preferably glycerine and/or sorbitol and/or xylitol. Water is present typically in amount of at least about 3% by weight; and glycerine and/or sorbitol and/or xylitol typically total about 6.5% to about 75% by weight of the oral preparation, more typically about 10% to about 75%, and, together with the solubilizing humectant, the essential humectant components typically amount to about 7% to about 80% by weight of the oral preparation. Reference hereto to sorbitol refers to the material typically as available commercially in about 70% aqueous solutions. Where the composition contains a substantially water insoluble noncationic anti-bacterial agent, the composition will preferably be free of at least significant amounts of polyethylene glycol, particularly of average molecular weight of about 600 or more, since polyethylene glycol can inhibit the antibacterial activity of a noncationic antibacterial agent, even when another component, such as, propylene glycol is present to effect its solubilization.

The vehicle can also be a water-alcohol mixture. Generally, the weight ratio of water to alcohol is in the range of from about 1:1 to about 20:1, preferably about 3:1 to about 10:1 and more preferably about 4:1 to about 6:1. The total amount of water-alcohol mixture in, for example, a mouthwash is typically in the range of from about 70 to about 99.9% by weight. The alcohol is a non-toxic alcohol such as ethanol or isopropanol. A humectant, such as glycerine, sorbitol, or xylitol may be present in an amount of about 10 to about 30% by weight. The oral composition may contain water at about 5% to about 30% by weight. Liquid dentifrices typically contain about 50% to about 85% of water, may contain about 0.5% to about 20% by weight of non-toxic alcohol and may also contain about 10% to about 40% by weight of humectant, such as glycerine, sorbitol, and/or xylitol. Sorbitol refers to the material typically available commercially in about 70% aqueous solutions. Ethanol is the preferred non-toxic alcohol. The alcohol assists in dissolving the *Camellia* extract and the water-insoluble non-cationic anti-bacterial agent.

It may be desirable to include within the dentifrice composition one or more therapeutic agents that prevent, treat and/or reduce the symptoms related to various oral or systemic diseases or conditions. Useful therapeutic agents include all those known or developed in the art including steroids, NSAIDs, a fluoride ion source, polycarboxylate polymers, polyvinyl methyl ether/maleic anhydride (PVME/MA) copolymers, an arginine ester, a zinc ion source, a stannous ion source, delmopinol, tartar control agents, an antibacterial agent, triclosan and salts thereof, chlorhexidine, alexidine, hexetidine, sanguinarine, benzalkonium chloride, salicylanilide, domiphen bromide, cetylpyridinium chloride (CPC), tetradecylpyridinium chloride (TPC), N-tetradecyl-4-ethylpyridinium chloride (TDEPC), octenidine, octapinol, nisin, a zinc ion source, a copper ion source, an essential oil, a furanone, anti-inflammatory agents, antiplaque agents, antioxidants, and a bacteriocins, and salts thereof, honokiol, vitamins, anti-attachment agents, proteinaceous agents, peptides. A further illustrative list of useful antibacterial agents is provided in U.S. Pat. No. 5,776,435, the contents of which are incorporated herein by reference.

The compositions of the present invention optionally comprise an antimicrobial (e.g., antibacterial agent). One or more such agents can be present. A particularly suitable non-ionic antibacterial agent is a diphenyl ether such as 2,4,4'-trichloro-2'-hydroxyether (Triclosan). The one or more antimicrobial agents are optionally present in an antimicrobial effective total amount, for example, from about 0.001% to about 10%, from about 0.01% to about 5% or from about 0.1% to about 3%.

In various embodiments, the anti-bacterial agent is a halogenated diphenyl ether, preferably 2,4,4'-trichloro-2'-hydroxyether (Triclosan). Triclosan can be present in the oral composition in various amounts, such as from about 0.001% to about 5%, or about 0.01% to about 3% by weight, or about 0.25% to about 0.35% by weight.

Abrasives may be added to the dentifrice formulation if desired. Any suitable oral care abrasive or polishing agent may be used. Preferred may be silica abrasives such as precipitated silicas, sodium metaphosphate, potassium metaphosphate, tricalcium phosphate, dihydrated dicalcium phosphate, aluminum silicate, calcined alumina, bentonite or other siliceous materials, particulate thermosetting resins, such as melamine, phenolic, and urea-formaldehydes, and cross-linked polyepoxides and polyesters.

As desired, any other additives may be included in the dentifrice composition for reasons of e.g., manufacturing, stability, aesthetics, therapeutic effect, consumer appeal, etc. Exemplary additives include all other conventional dentifrice additives, viscosity modifiers, diluents, foam modulators, saliva stimulating agents, desensitizing agents, whitening agents, enzymes, pH modifying agents, mouth-feel agents, sweeteners, colorants, opacifiers, and breath freshening agents.

The present invention provides for methods and processes of using the oral compositions of the present invention to treat and inhibit oral conditions, such as oral inflammatory conditions, dental plaque deposits on the teeth and oral tissues, and dental calculus. Further, the oral compositions can serve as antioxidants. The present invention provides for commercial packaging for the oral compositions to distribute and store the oral compositions.

The oral compositions can be applied to the subject in any suitable manner, as is known in the art. For example, the oral compositions can be applied to the subject's oral cavity using a suitable applicator or delivery device, such as a brush, dental strip, film, syringe, tape, gum, pill, or any other applicator or delivery device that is known in the art. The compositions can be used in prophylactic methods and processes to promote and maintain oral health, appearance, and breath freshness. The oral compositions can be repeatedly applied to the subject over a number of days according to a particular treatment schedule to treat and/or inhibit dental plaque deposits, dental calculus deposits, and oral inflammatory conditions and to provide anti-oxidant activity. Instructions setting forth the treatment schedule can be provided with the commercial packaging.

The present invention is further illustrated through the following non-limiting examples.

Example 1

A powder and/or oil extract is obtained from *Camellia sinensis*. The extract is commercially available from, for example, and Sabinsa, Corp. and can be Sabinsa specification no. MS-0726-01. The *Camellia* extract can include at least about 30% epigallocatechin gallate, at least about 50% total catechins, and at least about 60% total polyphenols. The extract is introduced to an in vitro cell culture assay system of human embryonic palatal messenchyme cells stimulated with IL1β. Prostaglandin E2 (PGE2) production is measurably inhibited when the extract is introduced to the assay. PGE2 is known to cause inflammation. Therefore, use of the extract to inhibit PGE2 production advantageously reduces and inhibits inflammation.

Example 2

Solution containing the anti-inflammatory Triclosan and the *Camellia* extract is prepared. The *Camellia* extract is present at a concentration below that required for the *Camellia* extract to act as an anti-inflammatory agent alone. The solution exhibits increased anti-inflammatory activity as compared to solutions of Triclosan alone. Therefore, *Camellia* extract advantageously acts synergistically with Triclosan to enhance the anti-inflammatory effect of Triclosan.

Example 3

The *Camellia* extract is included in an oral care product at various concentrations, such as a dentifrice at about 0.01%, about 10%, or any concentration between about 0.01% and about 10%, along with one or more suitable surfactants. The oral care product may also include concentrations of Triclosan and/or rosemary extract.

Example 4

The *Camellia* extract is included in an oral care product at various concentrations, such as an oral care portable strip at 0.1%, 0.2%, or any concentration between 0.1% and 0.2%, along with one or more suitable surfactants. The oral care strip is introduced into an in vitro system containing lipid peroxides undergoing oxidation. The oral care strip advantageously reduces the oxidation of lipid peroxides in vitro to provide antioxidant activity.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

We claim:

1. An oral composition in the form of a dental strip, said dental strip comprising:
   about 0.1% to about 0.2% by weight of a *Camellia* extract, said extract including at least about 30% epigallocatechin gallate, at least about 50% total catechins, and at least about 60% total polyphenols;
   about 0.1% to about 0.3%, by weight of 2',4,4'-trichloro-2-hydroxy-diphenyl ether, and
   a surfactant,
   wherein the *Camellia* extract is present in the oral composition in an amount that is less than the minimum amount of the *Camellia* extract that exhibits anti-inflammatory activity when the *Camellia* extract is present as the sole component therein having anti-inflammatory activity.

2. The composition according to claim 1, further comprising Vitamin E, wherein the Vitamin E is present in the composition in an amount of about 0.1% to about 4% by weight.

3. The composition according to claim 2, wherein the Vitamin E is present in the oral composition in an amount of about 0.2% to about 2.5% by weight.

4. A composition according to claim 1, wherein the *Camellia* extract is an extract of *Camellia sinensis* tissue.

5. A composition according to claim 1, wherein the *Camellia* extract is obtained from tissue of at least one of *Camellia sinensis* var. *assamica, Camellia sinensis* var. *cambodiensis, Camellia sinensis* var. *dehungensis, Camellia sinensis* var. *pubilimba*, and *Camellia sinensis* var. *sinensis*.

6. A composition according to claim 1, wherein the oral composition further comprises at least one botanical extract which is a rosemary extract.

7. The composition of claim 1, further comprising about 0.001% to about 5% by weight of Vitamin E, wherein the Vitamin E is dl-α-tocopherol.

8. The composition of claim 1, wherein the surfactant is selected from the group consisting of anionic, nonionic, amphoteric, zwitterionic, and cationic synthetic detergents.

9. The composition of claim 8, wherein the anionic surfactant is selected from the group consisting of sodium lauryl sulfate, sodium coconut monoglyceride sulfonate, sodium and potassium salts of lauroyl sarcosinate, myristoyl sarcosinate, palmitoyl sarcosinate, stearoyl sarcosinate, oleoyl sarcosinate, sodium lauryl sulfoacetate, sodium lauroyl isothionate, sodium laureth carboxylate, sodium dodecyl benezesulfonate, and mixtures thereof.

10. The composition of claim 8, wherein the nonionic surfactant is selected from the group consisting of poloxamers; polyoxyethylene sorbitan esters; fatty alcohol ethoxylates; polyethylene oxide condensates of alkyl phenols and mixtures thereof.

11. The composition of claim 8, wherein the amphoteric surfactant is cocamidopropylbetaine.

12. The composition of claim 8, wherein the cationic surfactant is selected from the group consisting of lauryl trimethylammonium chloride, cetylpyridinium chloride, cetyltrimethylammonium bromide, diisobuytylphenoxyethyldimethyl-benzylammonium chloride, coconut alkyltrimethylammonium nitrite, cetylpyridinium fluoride and mixtures thereof.

13. The composition of claim 1, wherein the surfactant is present in an amount of from about 0.02% to about 50% by weight.

\* \* \* \* \*